US009642918B2

(12) United States Patent
Bruederle et al.

(10) Patent No.: US 9,642,918 B2
(45) Date of Patent: May 9, 2017

(54) COMBINATION OF INOTUZUMAB OZOGAMICIN AND TORISEL FOR THE TREATMENT OF CANCER

(71) Applicants: Pfizer Inc., New York, NY (US); ONCOLOGY INSTITUTE OF SOUTHERN SWITZERLAND, Bellinzona (CH)

(72) Inventors: Andreas Bruederle, Potsdam (DK); Padraig Moran, Dublin (IE); Anastasios Stathis, Bellinzona (CH)

(73) Assignees: Pfizer Inc., New York, NY (US); Oncology Institute of Southern Switzerland (CH)

( * ) Notice: Subject to any disclaimer, the term of this patent is extended or adjusted under 35 U.S.C. 154(b) by 0 days.

(21) Appl. No.: 14/365,793

(22) PCT Filed: Dec. 4, 2012

(86) PCT No.: PCT/IB2012/056958
§ 371 (c)(1),
(2) Date: Jun. 16, 2014

(87) PCT Pub. No.: WO2013/088304
PCT Pub. Date: Jun. 20, 2013

(65) Prior Publication Data
US 2014/0335109 A1 Nov. 13, 2014

Related U.S. Application Data

(60) Provisional application No. 61/576,831, filed on Dec. 16, 2011.

(51) Int. Cl.
*A61K 31/436* (2006.01)
*A61K 31/704* (2006.01)
*A61K 39/395* (2006.01)
*A61K 47/48* (2006.01)
*C07K 16/28* (2006.01)
*C07K 16/30* (2006.01)

(52) U.S. Cl.
CPC ...... *A61K 47/48407* (2013.01); *A61K 31/436* (2013.01); *A61K 31/704* (2013.01); *A61K 39/39558* (2013.01); *C07K 16/2803* (2013.01); *C07K 16/3061* (2013.01)

(58) Field of Classification Search
None
See application file for complete search history.

(56) References Cited

U.S. PATENT DOCUMENTS

| | | |
|---|---|---|
| 3,929,992 A | 12/1975 | Sehgal |
| 3,993,749 A | 11/1976 | Sehgal |
| 4,401,653 A | 8/1983 | Eng |
| 4,885,171 A | 12/1989 | Surendra |
| 4,970,198 A | 11/1990 | Lee |
| 5,053,394 A | 10/1991 | Ellestad |
| 5,206,018 A | 4/1993 | Sehgal |
| 5,362,718 A | 11/1994 | Skotnicki |
| 2011/0226650 A1* | 9/2011 | Gokarn ............... A61K 9/0019 206/438 |

FOREIGN PATENT DOCUMENTS

| | | |
|---|---|---|
| EP | 0252960 | 2/1993 |
| WO | 2007/125252 | 11/2007 |
| WO | 2007/131689 | 11/2007 |

OTHER PUBLICATIONS

Serajuddin et al, Advanced Drug Delivery Reviews, 2007, vol. 59, pp. 603-161.*
Advani et al (Journal of Clinical Oncology, 2010, vol. 28, pp. 2085-2093).*
The abstract of Smith et al (Journal of Clinical Oncology, 2008, vol. 26, No. 15S (May 20 Supplement), p. 8514).*
Baker, H., et al., "Rapamycin (AY-22,989), A New Antifungal Antibiotic," Journal of Antibiotics, 1978, vol. 31, No. 6:, 539.
Berge, S., et al., "Pharmaceutical Salts," J. Pharm. Sci., 1977;66:1 19.
Devesa, S., et al., "Cancer Incidence and Mortality Trends Among Whites in the United States, 1947-84," J. Nat'l Cancer Inst., 1987, 79:701.
DiJoseph, J., et al., "Antibody-targeted chemotherapy with CMC-544: a CD22-targeted immunoconjugate of calicheamicin for the treatment of B-lymphoid malignancies," Blood 2004; 103:1807-1814.
Hamann, P., et al., "An Anti-CD33 Antibody-Calicheamicin Conjugate for the Treatment of Acute Myeloid Leukemia. Choice of Linker," Bioconjugate Chemistry, 2002; vol. 13:40-46.
Hirschfeld, S., et al., "Oncology drug development: United States Food and Drug Administration perspective" Critical Reviews in Oncology/Hematology, 2001, 42:137-143.
International Preliminary Report on Patentability dated Jun. 17, 2014, for International Application No. PCT/IB2012/056958.
Sehgal, S. et al., "Rapamycin (AY-ww,989), A New Antifungal Antibiotic" Journal of Antibiotics, 1975, vol. 28, 727.
Vezina, C., et al., "Rapamycin (EY-22,989), A New Antifungal Antiobiotic", Journal of Antibiotics, 1975, vol. 28, 721.
Zein, N., et al., "Calicheamicin Y1I: An Antitumor Antibiotic That Cleaves Double-Stranded DNA Site Specifically," Science, 1988; 240: 1198-1201.
DiJoseph J., et al., Antitumor efficacy of a comination of cmc-544 (inotuzumab ozogamicin), a CD22-Targeted Cytotoxic Immunoconjugate of Calicheamicin, and REtuximab against non-hodgkin's B-Cell Lymphoma, The American Association for Cancer Research, 2006, vol. 12:242-249.

(Continued)

Primary Examiner — Karen Canella
(74) Attorney, Agent, or Firm — Fariba Shoarinejad

(57) ABSTRACT

The present invention relates to a therapeutic method for the treatment of cancer that comprises the use of a combination of inotuzumab ozogamicin (CMC-544) and temsirolimus. The enhanced antitumor of the combination therapy is particularly useful for patient population that are recalcitrant to inotuzumab ozogamicin or temsirolimus therapy, relapse after treatment with inotuzumab ozogamicin or temsirolimus or where enhanced antitumor effect reduces toxicities associated with treatment using inotuzumab ozogamicin or temsirolimus.

3 Claims, No Drawings

(56) References Cited

OTHER PUBLICATIONS

International Search Report including the written opinion and dated May 14, 2013, for International Application No. PCT/IB2012/056958.

Kobayashi, Y., Molecular Target Therapy in Hematological Malignancy: Front-runners and Prototypes of Small Molecule and Antibody Therapy, Japanese Journal of Clinical Oncology, 2001, vol. 41:157-164.

Sessa C., Study of Inotuzumab Ozogamicin + Temsirolimus in Patients With Relapsed or Refractory CD22+ B-cell NHLymphoma Internet 2013.

Sessa C., Study of Inotuzumab Ozogamicin + Temsirolimus in Patients with Relapsed or Refractory CD22+ B-cell NHLymphoma Internet, 2011.

Tay, K. et al., Novel agents for B-cell non-Hodgkin lymphoma: Science and the promise, Blood Reviews, 2010, vol. 24:69-82.

\* cited by examiner

COMBINATION OF INOTUZUMAB OZOGAMICIN AND TORISEL FOR THE TREATMENT OF CANCER

CROSS-REFERENCE TO RELATED APPLICATIONS

This application is a §371 filing of PCT/IB2012/056958 filed Dec. 4, 2012, which claims the benefit of U.S. U.S. Provisional Application No. 61/576,831 filed Dec. 16, 2011, which is hereby incorporated by reference in their entireties.

FIELD OF THE INVENTION

This invention relates to a method of treating abnormal cell growth such as cancer by administering a combination of inotuzumab ozogamicin (CMC-544) and temsirolimus (rapamycin 42-ester with 3-hydroxy-2-(hydroxymethyl)-2-methylpropionic acid; CCI-779). In a particular embodiment, the present invention relates to a product comprising inotuzumab ozogamicin and temsirolimus for simultaneous, separate, or sequential use thereof for the prevention, delay of progression, and/or treatment of a proliferative disease, especially cancer.

BACKGROUND OF THE INVENTION

B cells are a critical component of the immune response in mammals, as they are the cells responsible for antibody production (humoral immunity). B cells are quite diverse, and this diversity is critical to the immune system. Each B cell within the host expresses a different antibody—thus, one B cell will express antibody specific for one antigen, while another B cell will express antibody specific for a different antigen. In humans, each B cell can produce an enormous number of antibody molecules (i.e., about $10^7$ to $10^8$). The maturation of B cells (and thus antibody production) most typically ceases or substantially decreases when the foreign antigen has been neutralized. Occasionally, however, proliferation of a particular B cell or plasma cell will continue unabated; such proliferation can result in a cancer referred to as "B cell lymphoma or multiple myeloma."

B cell lymphomas include both Hodgkin's lymphoma and a broad class of non-Hodgkin's lymphoma. Cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., J. Nat'l Cancer Inst. 79:701 (1987).

Non Hodgkin's lymphomas (NHL) are the most common hematologic malignancies in adults representing the sixth most commonly diagnosed cancer in North America and in Europe. Approximately 85% of NHL are of B-cell origin and comprise a heterogeneous group of malignancies, ranging from slow growing indolent and usually incurable diseases, to more aggressive but potentially curable lymphomas. CD22 is expressed in ~60% to >90% of B-lymphoid malignancies of the majority of NHLs with B-cell origin.

Over the past two decades, major progress has been achieved in the management of NHL. The introduction of rituximab, a monoclonal antibody directed against the B-cell surface antigen CD20, has significantly improved treatment outcomes in most patients with NHL. Rituximab in combination with standard chemotherapy has improved response rate, progression free and overall survival in both indolent and aggressive lymphomas.

Despite therapeutic advances, treatment is still challenging for many patients with lymphomas. Traditional methods of treating B-cell malignancies, including chemotherapy and radiotherapy, have limited utility due to toxic side effects. Most lymphomas respond initially to any one of the current chemotherapeutic agents, but tumors typically recur and eventually become refractory. As the number of regimens patients receive increases, the more chemotherapy resistant the disease becomes. Average response to first line therapy is approximately 75%, 60% to second line, 50% to third line, and 35-40% to fourth line. Response rates with a single-agent in the multiple relapsed setting approaching 20% are considered positive and warrant further study.

Additionally, the period of remission following each treatment decreases. Patients with indolent lymphomas will invariably relapse and many will require additional treatments, while more than half of the patients with aggressive lymphomas will not be cured following standard treatments. In fact, many patients with diffuse large B-cell lymphoma (the most common subtype of aggressive lymphomas) are refractory to standard chemotherapy and/or chemoimmunotherapy regimens and relapses are frequent even in patients that achieve an initial response to treatment.

The prognosis for those affected by these diseases is poor, as the survival rates for lymphoma patients remain low. Salvage approaches based on high-dose chemotherapy with stem-cell transplantation are helpful only for selected patients and most patients succumb to their disease or to complications of intensive treatments. New methods for treating these diseases are needed.

Therefore, there is a need for the development of novel agents and treatment regimens with less toxicity and more specific targeting of tumor cells. Targeted therapies provide a promising alternative to standard cytotoxic chemotherapy. Unlike traditional chemotherapy, they affect specific targets present in the lymphoma cells and may spare normal tissues, thus minimize toxicity. The combination of agents that target specific components of pathways relevant to lymphomagenesis, with novel monoclonal antibodies represents a novel approach for the development of new treatment strategies in patients that are newly diagnosed, relapse or are refractory to Rituximab and standard chemotherapy.

Immunoconjugates comprising a member of the potent family of antibacterial and antitumor agents, known collectively as the calicheamicins or the LL-E33288 complex, (see U.S. Pat. No. 4,970,198 (1990)), were developed for use in the treatment of myelomas. The most potent of the calicheamicins is designated $\gamma_1$, which is herein referenced simply as gamma. These compounds contain a methyltrisulfide that can be reacted with appropriate thiols to form disulfides, at the same time introducing a functional group such as a hydrazide or other functional group that is useful in attaching a calicheamicin derivative to a carrier. (See U.S. Pat. No. 5,053,394). The use of the monomeric calicheamicin derivative/carrier conjugates in developing therapies for a wide variety of cancers has been limited both by the availability of specific targeting agents (carriers) as well as the conjugation methodologies which result in the formation of protein aggregates when the amount of the calicheamicin derivative that is conjugated to the carrier (i.e., the drug loading) is increased. Inotuzumab ozogamicin (CMC544) is a CD22-specific immunoconjugate of calicheamicin in which a humanized IgG4 anti-CD22 mAb, G5/44, is covalently linked via an acid-labile AcBut linker to CalichDMH (Blood 2004; 103:1807-1814). CalichDMH (N-acetyl gamma calicheamicin dimethylhydrazide) is a derivative of gamma calicheamicin, a DNA-damaging enediyne antibiotic (Bioconj Chem 2002; 13:40-46). Gamma calicheamicin binds DNA in the minor groove and with the help of cellular thiols brings about double-strand DNA breaks (Science 1988; 240: 1198-1201) leading to cellular apoptosis and cell death. Antibody-targeted chemotherapy enables a cytotoxic agent to be delivered specifically to tumor cells by conjugating the cytotoxic agent with a monoclonal antibody that binds to a tumor-associated antigen. This strategy preferentially delivers the cytotoxic agent to tumor cells, minimizes exposure of normal tissues (lacking the targeted agent) to the cytotoxic agent, and results in a significantly improved therapeutic index.

Temsirolimus is a specific inhibitor of the mammalian target of rapamycin (mTOR), an enzyme that regulates cell growth and proliferation. Temsirolimus prevents progression from the G1 phase to the S phase of the cell cycle through inhibition of mTOR. The mTOR is a kinase that propagates signalling through growth factor pathways and regulates metabolic pathways that allow tumors to adapt to a harsh microenvironment. Inhibitors of mTOR, therefore, have the potential to inhibit tumor cell growth on at least two levels, a direct inhibitory effect on mutated growth factor signaling pathways and an indirect effect through inhibition of mTOR-regulated tumor survival factors.

Temsirolimus (CCI-779, rapamycin 42-ester with 3-hydroxy-2-(hydroxymethyl)-2-methylpropionic acid) is a structural analog of sirolimus (rapamycin) that has been formulated for IV or oral administration for the treatment of various malignancies. Temsirolimus is an antineoplastic agent. Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

Rapamycin is useful in preventing or treating adult T-cell leukemia/lymphoma [European Patent Application 525,960 A1] and malignant carcinomas [U.S. Pat. No. 5,206,018]. The preparation and use of hydroxyesters of rapamycin, including CCI-779, are disclosed in U.S. Pat. No. 5,362,718.

For patients with lymphomas relapsed or refractory to standard chemotherapy, improvements in outcomes may derive from the development of alternative treatment strategies with less toxicity and better targeting of the lymphoma cells. Basic and preclinical laboratory research have permitted to identify some of the pathways that are abnormally expressed in lymphomas and agents that target specific components of these pathways have entered clinical evaluation in recent years. While some of these agents have proven to be effective and associated with a better toxicity profile than standard chemotherapy, resistance has been often observed, limiting their clinical use.

The increase of the antitumor efficacy of a known antitumor compound by administering the same in combination with one or more different antitumor drugs in order to reduce the toxic effects of the individual agents when used alone, and because the combination has greater efficacy than when either agent is used alone, is a strongly felt need in the field of anticancer therapy. Moreover, improved anti-cancer therapies comprise a large unmet medical need and the identification of novel systemic therapies and combination regimens are required to improve treatment outcome by targeting all types of B cell malignancies. In particular, there is a need for a therapy which can overcome the shortcomings of current treatments regimens by using combination of immunoconjugates and small molecules to treat a variety of malignancies including hematopoietic malignancies like non-Hodgkin's lymphoma (NHL), without inducing an immune response. Such improved therapy has the advantage of targeting a diverse group of B cell malignancies by using two agents with different mechanism of actions. Further, non-Hodgkin lymphomas are a diverse group of blood cell cancers derived from lymphocytes, a type of white blood cell. As such, patients with different types of B-cell non Hodgkins lymphomas would benefit from the combination therapy of the present invention.

Moreover, the combination therapy of the present invention is potentially more effective and less toxic; and thus allows repeated administration of comparatively low dosage levels of two or more agents targeting different types of B-cell malignancies and for longer periods of treatment.

In addition to treating newly diagnosed patients, the novel combination therapy using combinations of targeted agents, such as ADCs, with a cytotoxic agent represents possible approach to overcome resistance that may be developed to treatment. Further, the enhanced antitumor activity of the combination therapy is particularly useful for patient population that relapse after treatment with inotuzumab ozogamicin or temsirolimus alone or where enhanced antitumor effect reduces toxicities associated with treatment using inotuzumab ozogamicin or temsirolimus alone. Accordingly, the present invention provides methods for enhancing the antitumor activity of inotuzumab ozogamicin and temsirolimus by a novel combination and sequential therapy regimen.

SUMMARY OF THE INVENTION

The present invention provides pharmaceutical composition comprising an amount of inotuzumab ozogamicin or a pharmaceutically acceptable salt thereof; an amount of temsirolimus or a pharmaceutically acceptable salt thereof; and a pharmaceutically acceptable carrier or diluent.

In one embodiment, the present invention provides a first pharmaceutical composition for use with a second pharmaceutical composition for achieving an anti-cancer effect in a mammal suffering from cancer, which anti-cancer effect is greater than the sum of the anti-cancer effects achieved by administering said first and second pharmaceutical compositions separately, and which second pharmaceutical composition comprises an amount of temsirolimus or a pharmaceutically acceptable salt thereof and a pharmaceutically acceptable carrier or diluent, said first pharmaceutical composition comprising an amount of inotuzumab ozogamicin or a pharmaceutically acceptable salt thereof and a pharmaceutically acceptable carrier or diluent.

In another embodiment, the present invention provides a first pharmaceutical composition for use with a second pharmaceutical composition for achieving an anti-cancer effect in a mammal suffering from cancer, which anti-cancer effect is greater than the sum of the anti-cancer effects achieved by administering said first and second pharmaceutical compositions separately, and which second pharmaceutical composition comprises an amount of inotuzumab ozogamicin or a pharmaceutically acceptable salt thereof and a pharmaceutically acceptable carrier or diluent, said first pharmaceutical composition comprising an amount of temsirolimus or a pharmaceutically acceptable salt thereof and a pharmaceutically acceptable carrier or diluent.

In yet another embodiment, the present invention provides a first pharmaceutical composition for use with a second pharmaceutical composition for achieving an anti-cancer effect in a mammal suffering from cancer, which anti-cancer effect is greater than the anti-cancer effects achieved by administering said first and second pharmaceutical compositions separately, and which second pharmaceutical composition comprises an amount of temsirolimus or a pharmaceutically acceptable salt thereof and a pharmaceutically acceptable carrier or diluent, said first pharmaceutical composition comprising an amount of inotuzumab ozogamicin or a pharmaceutically acceptable salt thereof and a pharmaceutically acceptable carrier or diluent.

In another embodiment, the present invention provides a first pharmaceutical composition for use with a second pharmaceutical composition for achieving an anti-cancer effect in a mammal suffering from cancer, which anti-cancer effect is greater than the anti-cancer effects achieved by administering said first and second pharmaceutical compositions separately, and which second pharmaceutical composition comprises an amount of inotuzumab ozogamicin or a pharmaceutically acceptable salt thereof and a pharmaceutically acceptable carrier or diluent, said first pharmaceutical composition comprising an amount of temsirolimus or a pharmaceutically acceptable salt thereof and a pharmaceutically acceptable carrier or diluent.

A method of treating cancer comprising administering to a patient in need thereof an effective amount of a combination of inotuzumab ozogamicin and temsirolimus.

In another embodiment, the first and second pharmaceutical compositions of the present invention, wherein said anti-cancer effects are achieved against a cancer selected from hematologic malignancies, non-Hodgkin's lymphoma (NHL) including follicular NHL or aggressive NHL (predominantly diffuse large B-cell lymphoma [DLBCL]). Acute Myeloid leukaemia (AML), Chronic myeloid leukemia (CML), Acute Lymphoblastic leukaemia (ALL), B cell malignancies, and myelodysplastic syndrome, Myelo-dysplastic syndrome (MDS), myelo-proliferative diseases (MPD), Chronic Myeloid Leukemia (CML), T-cell Acute Lymphoblastic leukaemia (T-ALL), B-cell Acute Lymphoblastic leukaemia (B-ALL), lung cancer, small cell lung cancer, non-small cell lung cancer, brain cancer, glioblastoma, neuroblastoma, squamous cell cancer, bone cancer, pancreatic cancer, skin cancer, cancer of the head or neck, cutaneous or intraocular melanoma, uterine cancer, ovarian cancer, colorectal cancer, colon cancer, rectal cancer, cancer of the anal region, gastric cancer, stomach cancer, breast cancer, gynecological cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the large intestine, cancer of the endocrine system, cancer of the thyroid gland, cancer of the parathyroid gland, cancer of the adrenal gland, sarcoma of soft tissue, cancer of the urethra, cancer of the penis, testicular cancer, prostate cancer, chronic or acute leukemia, lymphocytic lymphomas, cancer of the bladder, cancer of the kidney or ureter, renal cell carcinoma, carcinoma of the renal pelvis, neoplasms of the central nervous system ("CNS"), primary CNS lymphoma, spinal axis tumors, brain stem glioma, pituitary adenoma, solid tumors of childhood or a combination of one or more of the foregoing cancers.

In yet another embodiment, the present invention provides for a kit for achieving a therapeutic effect in a mammal comprising a therapeutically effective amount of inotuzumab ozogamicin, or a pharmaceutically acceptable salt thereof, and a pharmaceutically acceptable carrier or diluent in a first unit dosage form; a therapeutically effective amount of and temsirolimus, or a pharmaceutically acceptable salt thereof and a pharmaceutically acceptable carrier or diluent in a second unit dosage form; and container means for containing said first and second dosage forms.

In another embodiment, the present invention provides for a dosage form for achieving a therapeutic effect in a mammal comprising therapeutically effective amount of inotuzumab ozogamicin, or a pharmaceutically acceptable salt thereof; atherapeutically effective amount of temsirolimus, or a pharmaceutically acceptable salt thereof; and one or more pharmaceutically acceptable carriers or diluents.

In yet another embodiment, the kits and the dosage form is for the treatment of cancer wherein the cancer is selected from hematologic malignancies, non-Hodgkin's lymphoma (NHL) including follicular NHL or aggressive NHL (predominantly diffuse large B-cell lymphoma [DLBCL]). Acute Myeloid leukaemia (AML), Chronic myeloid leukemia (CML), Acute Lymphoblastic leukaemia (ALL), B cell malignancies, and myelodysplastic syndrome, Myelo-dysplastic syndrome (MDS), myelo-proliferative diseases (MPD), Chronic Myeloid Leukemia (CML), T-cell Acute Lymphoblastic leukaemia (T-ALL), B-cell Acute Lymphoblastic leukaemia (B-ALL), lung cancer, small cell lung cancer, non-small cell lung cancer, brain cancer, glioblastoma, neuroblastoma, squamous cell cancer, bone cancer, pancreatic cancer, skin cancer, cancer of the head or neck, cutaneous or intraocular melanoma, uterine cancer, ovarian cancer, colorectal cancer, colon cancer, rectal cancer, cancer of the anal region, gastric cancer, stomach cancer, breast cancer, gynecological cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the large intestine, cancer of the endocrine system, cancer of the thyroid gland, cancer of the parathyroid gland, cancer of the adrenal gland, sarcoma of soft tissue, cancer of the urethra, cancer of the penis, testicular cancer, prostate cancer, chronic or acute leukemia, lymphocytic lymphomas, cancer of the bladder, cancer of the kidney or ureter, renal cell carcinoma, carcinoma of the renal pelvis, neoplasms of the central nervous system ("CNS"), primary CNS lymphoma, spinal axis tumors, brain stem glioma, pituitary adenoma, solid tumors of childhood or a combination of one or more of the foregoing cancers. A method of treating cancer, the method comprising the step of administering to a subject in need of such treatment, either simultaneously or sequentially, an effective amount of inotuzumab ozogamicin and temsirolimus.

In another embodiment, the present invention provides for a method of treating cancer, the method comprising the step of administering to a subject in need of such treatment, either simultaneously or sequentially, an effective amount of inotuzumab ozogamicin and temsirolimus.

In yet another embodiment, the present invention provides for a method for treating a subject in need of therapeutic treatment comprising administering to said subject an amount of inotuzumab ozogamicin or a pharmaceutically acceptable salt thereof; and an amount of a temsirolimus or a pharmaceutically acceptable salt thereof; wherein inotuzumab ozogamicin and temsirolimus are each independently administered, optionally together with one or more pharmaceutically acceptable carriers or diluents. In yet another embodiment, inotuzumab ozogamicin and temsirolimus are administered simultaneously. In yet another embodiment, inotuzumab ozogamicin and temsirolimus are administered concurrently.

In one embodiment, the present invention provides for a method of treating cancer wherein, inotuzumab ozogamicin is administered at a dose of 0.4 mg/m$^2$ to 1.8 mg/m$^2$ every 4 weeks for 6 cycles and temsirolimus is administered at a dose of 5 to 175 mg/week until disease progression. In one embodiment, the present invention provides for a method of treating cancer wherein inotuzumab ozogamicin and temsirolimus are administered up to 24 weeks. In another embodiment, the present invention provides for a method of treating cancer wherein the inotuzumab ozogamicin does is from 0.4 to 1.8 mg/m$^2$/dose. In another embodiment, the present invention provides for a method of treating cancer wherein the temsirolimus dose is from 10 to 175 mg/dose. In another embodiment, the present invention provides for a method of treating cancer wherein the inotuzumab dose is from 0.4 to 0.8 mg/m2 every 4 weeks. In yet another embodiment, the present invention provides for a method of treating cancer wherein the temsirolimus dose is 5 mg to 25 mg every week. In yet another embodiment, the present invention provides for a method of treating cancer wherein the temsirolimus dose starts on the day 8 of the treatment schedule.

In one embodiment, the present invention provides a pharmaceutical composition for treating cancer wherein the cancer is NHL or ALL.

In one embodiment, the present invention provides for a pharmaceutical composition suitable for treating cancer, comprising inotuzumab ozogamicin, and temsirolimus, in combination with one or more pharmaceutically acceptable carriers or vehicles, wherein the cancer is sensitive to the combination inotuzumab ozogamicin and temsirolimus, and wherein an anticancer effect is achieved with a combination of inotuzumab ozogamicin and temsirolimus which is larger than the anticancer effect achieved with either inotuzumab ozogamicin or temsirolimus alone and exceeds the sum of the effects of inotuzumab ozogamicin and temsirolimus.

In one embodiment, the present invention provides for a pharmaceutical composition suitable for treating cancer, comprising inotuzumab ozogamicin and temsirolimus in combination with one or more pharmaceutically acceptable carriers or vehicles, wherein inotuzumab ozogamicin and temsirolimus are combined or co-formulated in a single dosage form.

DETAILED DESCRIPTION OF THE INVENTION

The present invention relates to combinations of inotuzumab ozogamicin (CMC-544) and temsirolimus (rapamycin 42-ester with 3-hydroxy-2-(hydroxymethyl)-2-methyl-propionic acid; CCI-779), and to their use in the treatment of cancer. Additionally, the present invention also related to the combinations of inotuzumab ozogamicin and sirolimus (rapamycin). In a particular embodiment, the present invention relates to a pharmaceutical composition comprising inotuzumab ozogamicin and temsirolimus and optionally at least one pharmaceutically acceptable carrier for simultaneous, separate, or sequential use, in particular, for the treatment of B cell malignancies; the use of such a combination for the preparation of a medicament for the delay of progression or treatment of a proliferative disease, such as B cell malignancies; a commercial package or product comprising such a combination; and to a method of treatment of a warm-blooded animal, especially a human.

In particular, the present invention provides methods and compositions related to combination of two agents with different mechanism of action for treatment of B malignancies. In the present invention, the mTOR inhibitor, temsirolimus is administered in combination with inotuzumab ozogamicin, an antibody-targeted chemotherapy. Both agents have shown significant clinical activity in patients with relapsed/refractory lymphomas that progressed after several lines of standard treatments.

In certain embodiments, the combination therapy provides for the administration inotuzumab ozogamicin and temsirolimus.

Inotuzumab Ozogamicin:

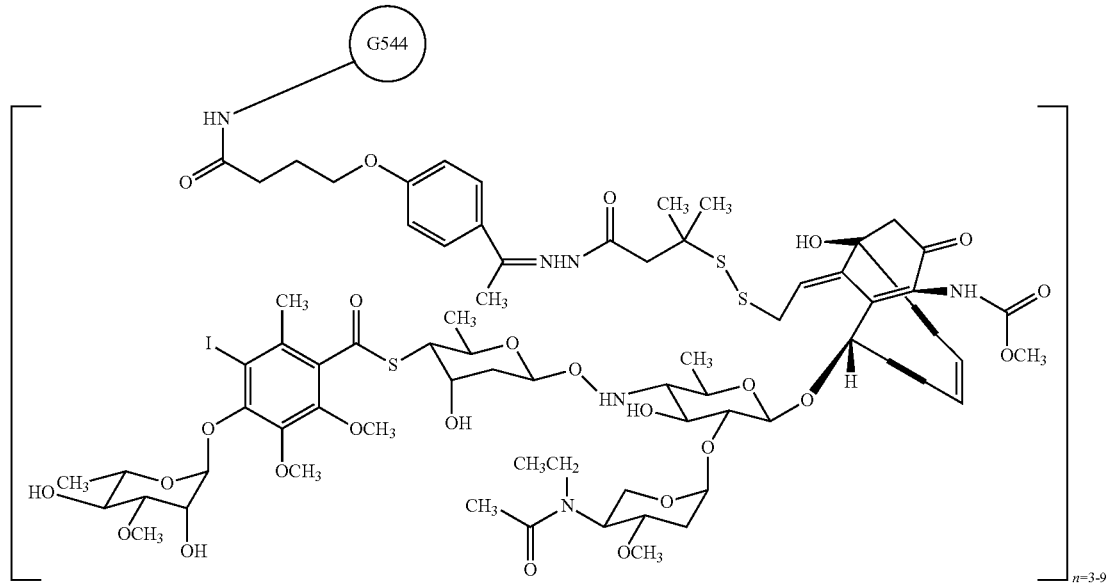

is described in U.S. patent application Ser. No. 10/428,894.
Temsirolimus (CCI-779):

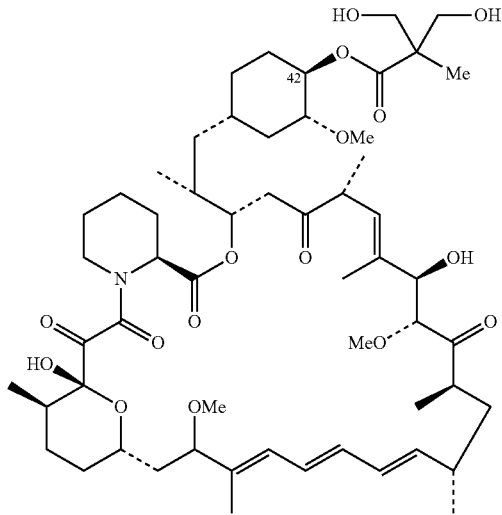 [SMILES: COC1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C(C)(CO)CO)[C@H](OC)C2)CC(=O)[C@H](C)/C=C(\C)[C@@H](O)[C@@H](OC)C(=O)[C@H](C)C[C@H](C)/C=C/C=C/C=C/1C]

is described in U.S. Pat. No. 5,362,718 which are incorporated herein by reference.

The term "therapeutically effective amount" means an amount of a compound or combination of compounds that treats a disease; ameliorates, attenuates, or eliminates one or more symptoms of a particular disease; or prevents or delays the onset of one of more symptoms of a disease.

The term "pharmaceutically acceptable", as used herein, means that a compound or combination of compounds is compatible with the other ingredients of a formulation, and not harmful for the patient or have acceptable risk benefit.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "a method of treating" or its equivalent, when applied to, for example, cancer refers to a procedure or course of action that is designed to reduce or eliminate the number of cancer cells in a patient, and/or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed an overall beneficial course of action.

The term, "anticancer therapy", as used herein, refers to all types of therapies for treating cancers or neoplasms or malignant tumors found in mammals comprising humans, including leukemia, lymphoma, melanoma, liver, breast, ovary, prostate, stomach, pancreas, lung, kidney, colon and central nervous system tumors.

The instant invention relates to a novel combination therapy using inotuzumab ozogamicin and temsirolimus which decrease cancer cell growth without increasing the toxicity profile compared to the individual drugs. Inotuzumab ozogamicin and temsirolimus produce the standard side effects of cancer chemotherapy when used alone at therapeutic doses. The novel combination therapy of the present invention provides a method where inotuzumab ozogamicin and temsirolimus are administered at lower doses with comparable efficacy and allow for more frequent dosing. Additionally, the combination therapy of the present invention may lessen the severity or the occurrence of side effects and/or may reduce the chance of drug resistance.

"Combination therapy" or administration "in combination with" one or more further therapeutic agents includes simultaneous, concurrent, and consecutive administration in any order. The administration of the constituents of the combined preparations of the present invention can be made simultaneously, separately or sequentially.

According to the present invention there is provided a method for the treatment of cancers, comprising the simultaneous, concurrent or consecutive administration of inotuzumab ozogamicin and temsirolimus. For example, inotuzumab ozogamicin can be administered before or after or simultaneously with temsirolimus.

The term simultaneous administration as used herein in relation to the administration of medicaments refers to the administration of medicaments such that the individual medicaments are present within a subject at the same time. In addition to the concomitant administration of medicaments (via the same or alternative routes), simultaneous administration may include the administration of the medicaments (via the same or an alternative route) at different times.

Although the simultaneous administration of inotuzumab ozogamicin, and temsirolimus, may be maintained throughout a period of treatment or prevention, anti-cancer activity may also be achieved by subsequent administration of one compound in isolation (for example, temsirolimus without inotuzumab ozogamicin following combination treatment, or alternatively inotuzumab ozogamicin, without temsirolimus following combination treatment.

Thus, a further embodiment of the invention is provided which is a method for the treatment of a cancer, comprising: (a) an initial treatment phase comprising the simultaneous administration of inotuzumab ozogamicin and temsirolimus; and (b) a subsequent treatment phase comprising the administration of inotuzumab ozogamicin without temsirolimus. Further, there is provided a method for the treatment of cancer, comprising: (a) an initial treatment phase comprising the simultaneous administration of inotuzumab ozogamicin and temsirolimus; and (b) a subsequent treatment phase comprising the administration of temsirolimus without inotuzumab ozogamicin.

In one embodiment, the dosage regimen is tailored to the particular of the patient's conditions, response and associate treatments, in a manner which is conventional for any therapy, and may need to be adjusted in response to changes in conditions and/or in light of other clinical conditions.

The patient can be any mammalian patient that suffers from a B cell malignancy. Preferably, the patient is a human or non-human primate, a dog, a cat, a horse, a cow, a goat, a sheep, a rabbit, or a rodent (e.g., mouse or rat). Those skilled in the medical art are readily able to identify individual patients who are afflicted with cancer and who are in need of treatment.

In one embodiment of this method, the abnormal cell growth is cancer, including, but not limited to, hematologic malignancies, non-Hodgkin's lymphoma (NHL), Acute Myeloid leukaemia (AML), Chronic myeloid leukemia (CML), Acute Lymphoblastic leukaemia (ALL), B cell malignancies, and myelodysplastic syndrome, Myelo-dysplastic syndrome (MDS), myelo-proliferative diseases (MPD), Chronic Myeloid Leukemia (CML), T-cell Acute Lymphoblastic leukaemia (T-ALL), B-cell Acute Lymphoblastic leukaemia (B-ALL), mesothelioma, hepatobilliary (hepatic and billiary duct), a primary or secondary CNS tumor, a primary or secondary brain tumor, lung cancer (NSCLC and SCLC), squamous cell cancer, bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal) cancers, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

This invention also relates to a method for the treatment of abnormal cell growth in a mammal which comprises administering to said mammal an amount of inotuzumab ozogamicin or salts or solvates thereof that is effective in treating abnormal cell growth in combination with temsirolimus.

The Bliss independence combined response C for two single compounds with effects A and B is C=A+B−A*B, where each effect is expressed as a fractional inhibition between 0 and 1. (Reference: Bliss (1939) *Annals of Applied Biology*) The Bliss value, defined to be the difference between the experimental response and the calculated Bliss Independence value, indicates whether the two compounds in combination are additive or synergistic.

A Bliss value of zero (0) is considered additive. The term "additive" means that the result of the combination of the two targeted agents is the sum of each agent individually.

The terms "synergy" or "synergistic" are used to mean that the response of the combination of the two agents is more than the sum of each agent's individual response. More specifically, in the in vitro setting one measure of synergy is known as "Bliss synergy." Bliss synergy refers to "excess over Bliss independence", as determined by the Bliss value defined above. When the Bliss value is greater than zero (0), or more preferably greater than 0.2, it is considered indicative of synergy. Of course, the use of "synergy" herein also encompasses in vitro synergy as measured by additional and/or alternate methods.

References herein to a combination's in vitro biological effects, including but not limited to anti-cancer effects, being greater than, or equal to, the sum of the combination's components individually, may be correlated to Bliss values. Again, the use of "synergy" herein, including whether a combination of components demonstrates activity equal to or greater than the sum of the components individually, may be measured by additional and/or alternate methods.

In measuring in vivo or therapeutic synergy one measure of synergy is known as "Excess over Highest Single Agent" Synergy. Excess over Highest Single Agent Synergy occurs where a combination of fixed doses is such that it is superior to both of its component doses then this is called "excess over highest single agent". (see FDA's policy at 21 CFR 300.50 which employs such method for approval of combination drug products; and, Borisy et al. (2003) *Proceedings of the National Academy of Science*). Of course, the use of "synergy" herein also encompasses in vivo synergy as measured by additional and/or alternate methods.

In measuring in vivo synergy one measure of synergy is known as "Excess over Highest Single Agent" Synergy. Excess over Highest Single Agent Synergy occurs where a combination of fixed doses is such that it is superior to both of its component doses then this is called "excess over highest single agent". (see FDA's policy at 21 CFR 300.50 which employs such method for approval of combination drug products; and, Borisy et al. (2003) *Proceedings of the National Academy of Science*). Of course, the use of "synergy" herein also encompasses in vivo synergy as measured by additional and/or alternate methods.

In one embodiment, the method of the invention is related to a method of treating cancer comprising administering to a patient in need thereof an effective amount of: (i) inotuzumab ozogamicin or a pharmaceutically effective salt, derivative or metabolite thereof in combination with an effective amount of temsirolimus or a pharmaceutically effective salt thereof, in amounts sufficient to achieve synergistic effects. In this embodiment, the method of the invention is related to a synergistic combination of the targeted therapeutic agents, inotuzumab ozogamicin and temsirolimus.

Certain aspects of the invention relates to the administration of inotuzumab ozogamicin or a pharmaceutically acceptable salt thereof; and temsirolimus or a pharmaceutically acceptable salt thereof. The term "pharmaceutically acceptable salt", as used herein, unless otherwise indicated, includes salts of acidic or basic groups which may be present in the compounds of the present invention. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," *J. Pharm. Sci.,* 1977; 66:1-19 which is incorporated herein by reference); and. Handbook of Pharmaceutical Salts, P. Heinrich Stahl, Camille G. Wermuth (Eds.), Published jointly by VHCA (Zurich, Switzerland) & Wiley-VCH (Weinheim, Germany) 2002.

Additionally inotuzumab ozogamicin and temsirolimus, and pharmaceutically acceptable acid addition salts thereof, may occur as hydrates or solvates, acid hydrates and solvates are also within the scope of the invention.

An effective amount or dosage of inotuzumab ozogamicin or temsirolimus, may be understood to comprise an amount sufficient to prevent or inhibit the growth of tumor cells or the progression of cancer metastasis in the combination of the present invention. Therapeutic or pharmacological effectiveness of the doses and administration regimens may also be characterized as the ability to induce, enhance, maintain or prolong remission in patients experiencing specific tumors.

Inotuzumab ozogamicin and temsirolimus may be used as a fixed-dosed combination product, Such fixed-dosed combination products, with inotuzumab ozogamicin and temsirolimus combined or co-formulated in a single dosage form, offers simplified treatment regimens, improved clinical effectiveness, enhanced patient adherence and reduced administrative costs. The fixed-dose combination of the present invention may include additional agents such as chemotherapeutic agents and/or anti CD-20 antibodies. For example, Rituxan can be combined or co-formulated in a single dosage form with inotuzumab ozogamicin and temsirolimus as a fixed-dosed combination product.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematology 42:137-143 2002).

Continued eligibility is assessed throughout the treatment on the basis of a continued acceptable risk/benefit ratio and signs of disease progression. Acceptable risk/benefit ratio may be determined by the Principal Investigator (PI) with confirmation by the Medical Monitor and/or Medical Advisor. Conditions that may warrant termination include the discovery of an unexpected, significant, or unacceptable risk to the subjects enrolled in the trial or failure to enroll subjects at an acceptable rate.

The appropriate effective amount or dosage of each compound, as used in the combination of the present invention, to administer to a patient, takes into account factors such as age, weight, general health, the compound administered, the route of administration, the nature and advancement of the cancer requiring treatment, and the presence of other medications.

Administration of the compounds of the combination of the present invention can be effected by any method that enables delivery of the compounds to the site of action. These methods include oral routes, intraduodenal routes, parenteral injection (including intravenous, subcutaneous, intramuscular, intravascular or infusion), Nasal/inhalational, topical, and rectal administration.

The compounds of the method or combination of the present invention may be formulated prior to administration. The formulation will preferably be adapted to the particular mode of administration. These compounds may be formulated with pharmaceutically acceptable carriers as known in the art and administered in a wide variety of dosage forms as known in the art. In making the pharmaceutical compositions of the present invention, the active ingredient will usually be mixed with a pharmaceutically acceptable carrier, complexed or diluted by a carrier or enclosed within a carrier. Such carriers include, but are not limited to, solid diluents or fillers, excipients, sterile aqueous media and various non-toxic organic solvents. Dosage unit forms or pharmaceutical compositions include tablets, capsules, such as gelatin capsules, pills, powders, granules, aqueous and nonaqueous oral solutions and suspensions, lozenges, troches, hard candies, sprays, creams, salves, suppositories, jellies, gels, pastes, lotions, ointments, injectable solutions, elixirs, syrups, and parenteral solutions packaged in containers adapted for subdivision into individual doses.

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Exemplary parenteral administration forms include solutions or suspensions of the compounds of the invention in sterile aqueous solutions, for example, aqueous propylene glycol or dextrose solutions. Such dosage forms can be suitably buffered, if desired.

Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

As used herein, a "pharmaceutically-acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, uses thereof in the compositions of the invention are contemplated. Supplementary active compounds can also be incorporated into the compositions.

In making the pharmaceutical compositions of the present invention, the active ingredient will usually be mixed or complexed with a pharmaceutically acceptable carrier, or diluted by a carrier or enclosed within a carrier. Such carriers include, but are not limited to, solid diluents or fillers, excipients, sterile aqueous media and various non-toxic organic solvents. Dosage unit forms or pharmaceutical compositions include tablets, capsules, such as gelatin capsules, pills, powders, granules, aqueous and nonaqueous oral solutions and suspensions, lozenges, troches, hard candies, sprays, creams, salves, suppositories, jellies, gels, pastes, lotions, ointments, injectable solutions, elixirs, syrups, and parenteral solutions packaged in containers adapted for subdivision into individual doses.

In particular, a therapeutically effective amount of inotuzumab ozogamicin and temsirolimus may be administered simultaneously or sequentially and in any order, and the components may be administered separately or as a fixed combination. For example, the method of delay of progression or treatment of a proliferative disease according to the invention may comprise: (a) administration of the inotuzumab ozogamicin in free or pharmaceutically acceptable salt form; and (b) administration of the temsirolimus in free or pharmaceutically acceptable salt form, simultaneously or sequentially in any order, in jointly therapeutically effective amounts, preferably in synergistically effective amounts, e.g., in daily or weekly dosages corresponding to the amounts described herein.

Inotuzumab ozogamicin and temsirolimus can be administered separately at different times during the course of therapy or concurrently in divided, single combination forms or fixed-dosed combination. The present invention is therefore to be understood as embracing all such regimes of simultaneous or alternating treatment and the term "administering" is to be interpreted accordingly.

The effective dosage of inotuzumab ozogamicin and temsirolimus may vary depending on the pharmaceutical composition employed, the mode of administration, the condition being treated and the severity of the condition being treated. Thus, the dosage regimen the combination therapy using inotuzumab ozogamicin and temsirolimus is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

Dosage units may be expressed in mg/kg (i.e. mg/kg of body weight), mg/week or $mg/m^2$. The $mg/m^2$ dosage units refer to the quantity in milligrams per square meter of body surface area. DLT refers to dose limiting toxicity.

The method according to the present invention may provide an improved level of anti-cancer activity suppression in comparison to conventional anti-cancer treatments comprising inotuzumab ozogamicin or temsirolimus alone. As such, it may be possible to utilize the anti-cancer agents of the invention at doses which would be insufficient (i.e. sub-therapeutic) in the absence of the other anti-cancer agent while maintaining the same or an adequate level of anti-cancer activity with fewer side effects.

In the method of the present invention, inotuzumab ozogamicin may be administered orally ("PO") in a dosage of about 0.4 to about 5 mg once daily ("QD"). For example, inotuzumab ozogamicin may be administered orally ("PO") in a dosage of about 0.4 to about 3 mg once daily ("QD"). In an embodiment, inotuzumab ozogamicin may be administered orally ("PO") in a dosage of about 0.8 or 1.8 mg once daily ("QD"), for instance 0.8, 1.3, and 1.8 mg once daily. In another embodiment, inotuzumab ozogamicin may be administered via IV infusion.

In the method of the present invention, inotuzumab ozogamicin may be administered in a dosage of about 0.4 to about 5 $mg/m^2$ via IV infusion once every 1 to 8 weeks. In particular, in the method of the present invention, inotuzumab ozogamicin may be administered in a dosage of about 0.4 to about 1.8 $mg/m^2$ via IV infusion over about 60 minutes once every 1 to 4 weeks. For example, inotuzumab ozogamicin may be administered in a dosage of about 0.4 to about 1.8 $mg/m^2$ via IV infusion every 1 or 4 weeks. In an embodiment, inotuzumab ozogamicin may be administered in a dosage of about 0.4 to about 0.8 $mg/m^2$. In another embodiment, inotuzumab ozogamicin may be administered in a dosage of about 0.4 to about 0.8 $mg/m^2$ every 4 weeks.

In the method of the present invention, temsirolimus may be administered via IV in a dosage of about 5 to about 175 mg per week. For example, temsirolimus may be administered orally ("PO") in a dosage of about 5 to about 75 mg per week. In an embodiment, temsirolimus may be administered via IV 5, 10, 15, 25, 50, 75, 100, 125, 150, and 175 mg/week. In another embodiment, temsirolimus may be administered orally ("PO") in a dosage of about 5 or 25 mg per week. In yet another embodiment, temsirolimus may be administered orally ("PO") in a dosage of about 5 or 25 mg every week.

Inotuzumab ozogamicin can be administered before, during or after the administration of temsirolimus. In an embodiment, inotuzumab ozogamicin is co-administered with temsirolimus, in separate dosage forms.

In some instances, dosage levels below the lower limit of the aforesaid range may be more than adequate, while in other cases still larger doses may be employed, as determined by those skilled in the art.

In some instances, inotuzumab ozogamicin and temsirolimus, is combined or co-formulated in a single dosage form.

The practice of the method of this invention may be accomplished through various administration regimens. In one aspect, the compounds may be administered in 1-week, 2-week, 3-week, 4-week, 5-week, 6-week, 7-week or 8-week cycles. In an embodiment, the compounds may be administered in 3-week cycles. Repetition of the administration regimens may be conducted as necessary to achieve the desired reduction or diminution of cancer cells. In a particular embodiment, temsirolimus is administered weekly and inotuzumab ozogamicin is administered every 4 weeks.

The present invention also provides pharmaceutical kits comprising one or more containers filled with one or more of the ingredients of the pharmaceutical compounds and/or compositions of the present invention, including, one or more immunoconjugates and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products. In particular, the invention relates to a kit comprising inotuzumab ozogamicin, temsirolimus, and written instructions for administration of the therapeutic agents. In one embodiment, the written instructions elaborate and qualify the modes of administration of the therapeutic agents, for example, for simultaneous or sequential administration of the therapeutic agents of the present invention. In another embodiment, the kit is for the treatment of cancer, including but not limited to hematologic malignancies, non-Hodgkin's lymphoma (NHL) including follicular NHL or aggressive NHL (predominantly diffuse large B-cell lymphoma [DLBCL]). Acute Myeloid leukaemia (AML), Chronic myeloid leukemia (CML), Acute Lymphoblastic leukaemia (ALL), B cell malignancies, and myelodysplastic syndrome, Myelo-dysplastic syndrome (MDS), myelo-proliferative diseases (MPD), Chronic Myeloid Leukemia (CML), T-cell Acute Lymphoblastic leukaemia (T-ALL), B-cell Acute Lymphoblastic leukaemia (B-ALL), lung cancer, small cell lung cancer, non-small cell lung cancer, brain cancer, glioblastoma, neuroblastoma, squamous cell cancer, bone cancer, pancreatic cancer, skin cancer, cancer of the head or neck, cutaneous or intraocular melanoma, uterine cancer, ovarian cancer, colorectal cancer, colon cancer, rectal cancer, cancer of the anal region, gastric cancer, stomach cancer, breast cancer, gynecological cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the large intestine, cancer of the endocrine system, cancer of the thyroid gland, cancer of the parathyroid gland, cancer of the adrenal gland, sarcoma of soft tissue, cancer of the urethra, cancer of the penis, testicular cancer, prostate cancer, cancer of the bladder, cancer of the kidney or ureter, renal cell carcinoma, carcinoma of the renal pelvis, neoplasms of the central nervous system ("CNS"), primary CNS lymphoma, spinal axis tumors, brain stem glioma, pituitary adenoma, solid tumors of childhood or a combination of one or more of the foregoing cancers.

In one embodiment, the present invention provides a non-randomized, open-labeled phase I study of inotuzumab ozogamicin in combination with temsirolimus in patients with CD22 positive relapsed/refractory NHL. In another embodiment, the present invention provides for a study which consists of a dose escalation part where patients with any type of CD22 positive NHL are enrolled to find the highest doses of inotuzumab ozogamicin and temsirolimus that can be given in combination. Once the Recommended Phase II Dose (RP2D) of the combination is established, 4 additional patients with any type of CD22 positive NHL are treated at the RP2D without further dose escalation (expansion cohort).

The results from the above descriptions and examples provide an improved method of cancer therapy that is expected to find widespread clinical utility. In particular, the results suggest that combination of inotuzumab ozogamicin and temsirolimus increases the multiple signals in tumor tissues by contributing to modulation of multiple pathways. Such novel combination therapy leads to a significant clinical anti-tumor effect.

The following Examples illustrate the invention described above; they are not, however, intended to limit the scope of the invention in any way. The beneficial effects of the combination therapy using can also be determined by other test models known as such to the person skilled in the pertinent art.

Example 1

Patient Selection

Patients have a histologically, and molecularly, and/or cytologically confirmed CD22 positive B-cell NHL, that is relapsed or refractory to standard treatments and for which standard curative or palliative measures do not exist or are no longer effective. Patients have measurable disease, defined as follows: clearly measurable (i.e. well defined boundaries) in at least two perpendicular dimensions on imaging scan; lymph node or nodal mass bi-dimensional measurement with >1.5 cm in longest transverse diameter.

There are no limitations on prior therapy. Patients may be newly diagnosed cancer patients and receive the treatment of the present invention as the first line therapy. The patients may also be non-responsive or develop resistance to chemotherapy and then experience disease relapse. Additionally, the methods of the present invention may be used to treat patients with relapsed/progressed after of cessation of any treatment by any anti-cancer drug.

However patients have discontinued any previous anti-cancer and investigational therapy including radiation therapy for at least 21 days prior to study drug, and have recovered fully from the side effects of such treatment prior to beginning study drug. Exceptions are made however, for low dose, non-myelosuppressive radiotherapy for symptomatic palliation. Patient are 18 years or older.

Patients who have prior therapy with an mTOR inhibitor or prior treatment with calicheamicin are excluded from the treatment.

Example 2

Treatment Plan

Treatments are administered on an outpatient basis. Appropriate dose modifications for inotuzumab ozogamicin and temsirolimus are described in Example 3. No investigational or commercial agents or therapies other than those described below are administered with the intent to treat the patient's lymphoma.

TABLE 1

Treatment plan

| Agent | Premedications; Precautions | Route | Schedule |
| --- | --- | --- | --- |
| Inotuzumab ozogamicin | No premedication required | IV infusion at a constant rate over a 1-hour (+/−15 minutes) period using a programmable infusion pump. | Day1 q28d |
| Temsirolimus | diphenhydramine 25 to 50 mg (or equivalent) approximately 30 minutes before the start of each dose of infusion | IV infusion over 30 minutes using a programmable infusion pump. | Days 1, 8, 15, 22q28d |

Inotuzumab ozogamicin is administered as an intravenous infusion on Day 1 of a 28 day cycle. The reconstituted and diluted admixture solution of the drug is administered within 4 hours of reconstitution for the 1 mg/vial dosage form and within 8 hours of reconstitution for the 3 mg/vial and 4 mg/vial dosage forms. Patients receive the admixture solution (total dose) by IV infusion at a constant rate over a 1-hour (+/−15 minutes) period using a programmable infusion pump. On day 1 of each cycle, inotuzumab ozogamicin is administered before the administration of temsirolimus.

No intrapatient dose escalation is permitted.

Temsirolimus is administered as an intravenous infusion on Days 1, 8, 15 and 22 of a 28 day cycle. Patients receive prophylactic medication of intravenous diphenhydramine 25 to 50 mg (or equivalent) approximately 30 minutes before the start of each dose of temsirolimus infusion. If a hypersensitivity/infusion reaction develops during the temsirolimus infusion, the infusion is stopped. Upon adequate resolution, and at the discretion of the physician, treatment is resumed with the administration of an H1-receptor antagonist (or equivalent), if not previously administered, and/or an H2-receptor antagonist (such as intravenous famotidine 20 mg or intravenous ranitidine 50 mg) approximately 30 minutes before restarting the temsirolimus infusion. The infusion is then be resumed at a slower rate (up to 60 minutes). Administration of the final diluted infusion solution is completed within six hours from the time that the concentrate diluent mixture is added to the sodium chloride injection. Temsirolimus concentrate-diluent mixture for injection is infused over a 30-60 minute period once a week. Preferably, an infusion pump is used for the administration to ensure accurate delivery of the drug.

On day 1 of each cycle, temsirolimus is administered approximately 1 hour after the end of the infusion of inotuzumab ozogamicin. No intrapatient dose escalation is permitted.

Example 3

Subject Dose Escalation

The study starts at dose level 1 and dose escalation of both drugs occurs as reported in table 2. If dose level 1 exceeds the recommended phase II dose (RPTD), the study will proceed with dose level −1.

TABLE 2 dose escalation scheme

| Dose Level | Inotuzumab Ozogamicin | Temsirolimus | Number of Patients |
|---|---|---|---|
| −1 | 0.8 mg/m$^2$ d1q28 | 10 mg d1, 8, 15, 22q28 | 3-6 |
| 1 | 0.8 mg/m$^2$ d1q28 | 15 mg d1, 8, 15, 22q28 | 3-6 |
| 2 | 1.3 mg/m$^2$ d1q28 | 15 mg d1, 8, 15, 22q28 | 3-6 |
| 3 | 1.3 mg/m$^2$ d1q28 | 25 mg d1, 8, 15, 22q28 | 3-6 |
| 4 | 1.8 mg/m$^2$ d1q28 | 25 mg d1, 8, 15, 22q28 | 3-6 |
| 5 | 1.8 mg/m$^2$ d1q28 | 50 mg d1, 8, 15, 22q28 | 3-6 |

Alternatively, the protocol is amended to skip the Day 1 dose of the temsirolimus.

TABLE 2B

Alternative dose escalation scheme

| Dose Level | Inotuzumab Ozogamicin | Temsirolimus | Number of Patients |
|---|---|---|---|
| 1 | 0.8 mg/m$^2$ d1q28 | 15 mg d 8, 15, 22q28 | 3-6 |

Based on the toxicities observed during the study, additional dose levels are explored, as reported in table 3.

TABLE 3

Additional dose levels

| Dose Level | Inotuzumab Ozogamicin | Temsirolimus | Number of Patients |
|---|---|---|---|
| −2a | 0.8 mg/m$^2$ d1q28 | 25 mg d1, 8, 15, 22q28 | 3-6 |
| −2b | 0.8 mg/m$^2$ d1q28 | 50 mg d1, 8, 15, 22q28 | 3-6 |
| −2c | 0.8 mg/m$^2$ d1q28 | 75 mg d1, 8, 15, 22q28 | 3-6 |

TABLE 3-continued

Additional dose levels

| Dose Level | Inotuzumab Ozogamicin | Temsirolimus | Number of Patients |
|---|---|---|---|
| −4a | 1.3 mg/m$^2$ d1q28 | 50 mg d1, 8, 15, 22q28 | 3-6 |
| −4b | 1.3 mg/m$^2$ d1q28 | 75 mg d1, 8, 15, 22q28 | 3-6 |

Based on current knowledge and due to the risk of cumulative toxicity, patients receive inotuzumab ozogamicin up to a maximum of 6 cycles. However, treatment approach is re-evaluated during the course of the study if patients are found to potentially benefit from additional inotuzumab ozogamicin treatment.

There is no planned limit on the maximum number of treatment cycles with temsirolimus. Dose escalation will proceed according to the following rules.

TABLE 4

Conventional 3 + 3 Dose Escalation Rule.

| Number of Patients with DLT at a Given Dose Level | Escalation Decision Rule |
|---|---|
| 0 out of 3 | Enter 3 patients at the next dose level |
| ≥2 | Dose escalation will be stopped. This dose level will be declared the maximally administered dose (highest dose administered). Three (3) additional patients will be entered at the next lowest dose level if only 3 patients were treated previously at that dose. |
| 1 out of 3 | Enter at least 3 more patients at this dose level. If 0 of these 3 patients experience DLT, proceed to the next dose level. If 1 or more of this group suffer DLT, then dose escalation is stopped, and this dose is declared the maximally administered dose. Three (3) additional patients will be entered at the next lowest dose level if only 3 patients were treated previously at that dose. |
| ≤1 out of 6 at highest dose level below the maximally administered dose | This is generally the recommended phase 2 dose. At least 6 patients must be entered at the recommended phase 2 dose. |

Patients are evaluated for DLT during the first 28 day cycle. All three patients treated on a dose level are observed for at least 28 days (one cycle) for any toxicity, and assessed for any DLT, before 3 other patients are entered on the same dose level or on next dose level. The RP2D is the dose at which ≤⅙ encountered DLT. Once the RP2D is established, 4 additional patients (up to a maximum of 10 patients) are treated in an expanded cohort at the RP2D. Intra-patient dose escalation is not permitted.

Example 4

Duration of Therapy

In the absence of treatment delays due to adverse events, treatment is continued until one of the following criteria applies: disease progression, inter-current illness that prevents further administration of treatment, unacceptable adverse events(s), patient decides to withdraw from the study, or general or specific changes in the patient's condition render the patient unacceptable for further treatment in the judgment of the investigator. Based on current knowledge and due to the risk of cumulative toxicity, patients receive inotuzumab ozogamicin up to a maximum of 6 cycles. However, treatment approach is re-evaluated during the course of the study if patients are found to potentially benefit from additional inotuzumab ozogamicin treatment.

Example 5

Dosing Delays and Dose Modification

Additional cycles of therapy are administered provided that the patient meets the following criteria on Day 1 of each cycle:

Absolute neutrophil count (ANC)≥1×10$^9$/L
Platelets (PLT)≥100×10$^9$/L
Non-hematologic toxicity recovered to ≤grade (Gr) 1 (or tolerable grade 2)
No evidence of progressive disease Study starts at dose level (DL) 1 (Table 2). If dose level 1 exceeds the RP2D, then study proceeds with dose level −1. Should a patient require a dose reduction during the study, dose levels are applied following tables 5a and 5b for inotuzumab ozogamicin and temsirolimus respectively.

TABLE 5A

General Guidance for Dose Reductions and Modifications-Inotuzumab Ozogamicin

| Current Inotuzumab Ozogamicin Dose | First Reduction | Second Reduction | Third Reduction |
|---|---|---|---|
| 1.8 mg/m$^2$ | 1.3 mg/m$^2$ | 0.8 mg/m$^2$ | Off Study |
| 1.3 mg/m$^2$ | 0.8 mg/m$^2$ | 0.4 mg/m$^2$ | Off study |
| 0.8 mg/m$^2$ | 0.4 mg/m$^2$ | Off study | — |
| 0.4 mg/m$^2$ | Off study | — | — |

TABLE 5B

General Guidance for Dose Reductions and Modifications-Temsirolimus

| Current Temsirolimus Dose | First Reduction | Second Reduction | Third Reduction |
|---|---|---|---|
| 75 mg | 50 mg | 25 mg | Off Study |
| 50 mg | 25 mg | 15 mg | Off study |
| 25 mg | 15 mg | 10 mg | Off study |
| 15 mg | 10 mg | Off study | — |
| 10 mg | Off study | — | — |

Day 1 dose modifications: If on day 1 of a new cycle patient has ANC <1.0 and/or Platelets <100 and/or non-hematologic toxicity grade 2 or higher, the treatment is delayed by one-week intervals (up to two weeks of delay are permitted) until recovery, then treat with: same dose as day 1 of previous cycle for neutropenia gr 3 or gr 4≤7 days, thrombocytopenia gr 3 or gr 4≤7 days and non hematologic adverse events grade ≤2. With one dose-level reduction of both drugs in case of febrile neutropenia, grade 4 hematologic adverse events lasting >7 days, bleeding associated thrombocytopenia within previous cycle and grade ≥3 non hematologic toxicities.

If day 1 dose of CMC-544 and/or CCI-779 is reduced, no dose re-escalation is allowed for the remainder of the study. Up to two dose reductions on day 1 are permitted.

Day 8, 15, 22 dose reductions: For temsirolimus dosing on days 8, 15 and 22, the following rules will apply:

| ANC (×10$^9$/L) | PLT (×10$^9$/L) | Non-hem AEs (see also Tables 6A-6C) | Dose |
|---|---|---|---|
| ≥1.0 | ≥75 | Gr 1 | 100% |
| ≥0.5 to <1.0 | ≥50 to <75 | Gr2 tolerable | Reduce by one DL |
| <0.5 | <50 | ≥Gr2 intolerable | Hold |

Patients requiring dose reductions should not have the dose re-escalated with subsequent treatments. However dose of temsirolimus may be re-escalated following a day 8, 15, 22 dose reduction, provided that ANC, Platelets and non hematologic adverse events have recovered to levels before day 1 of the previous cycle.

If a patient experiences several toxicities and there are conflicting recommendations, please use the recommended dose adjustment that reduces the dose to the lowest dose level. If an adverse event is not covered in section 6.2, doses are reduced or held at the discretion of the investigator for the subject's safety. Subjects with toxicities that are manageable with supportive therapy may not require dose reductions (e.g., nausea/vomiting may be treated with antiemetics). Subjects are withdrawn from the study if they fail to recover to common toxicity criteria (CTC) Grade 0-1 or tolerable grade 2 (or within 1 grade of starting values for pre-existing laboratory abnormalities) from a treatment-related toxicity within 14 days or they experience treatment-related adverse events requiring dose modification despite the number of permitted dose reductions (i.e. Tables 5a and 5b), unless the investigator agrees that the subject should remain in the study because of evidence that the patient is/may continue deriving benefit from continuing study treatment.

Specific Guidance for Dose Reductions and Modifications of temsirolimus based on Adverse Events is discussed in Tables 6A, 6B and 6C.

TABLE 6A

| | | Specific dose modifications for Metabolic/Laboratory. | |
|---|---|---|---|
| Adverse event | | National Cancer Institute (NCI) Common Terminology Criteria for Adverse Events (CTCAE) grade | Temsirolimus |
| Metabolic/Laboratory | | Cholesterol, serum high (hypercholesterolemia) ≥ Grade 3 Triglyceride, serum high (hypertriglyceridemia) Grade 1 and 2 | May continue treatment. Start or adjust dosage of antihyperlipidemic agents. If baseline levels, <grade 2 hypertriglyceridemia, or ≤ grade 2 hypercholesterolemia, |

TABLE 6A-continued

Specific dose modifications for Metabolic/Laboratory.

| Adverse event | National Cancer Institute (NCI) Common Terminology Criteria for Adverse Events (CTCAE) grade | Temsirolimus |
|---|---|---|
| | | whichever is higher, are not achieved after 8 weeks, discontinue agent. |
| | Triglyceride, serum high (hypertriglyceridemia) >Grade 3 | Omit temsirolimus for 1 week. Therapy with a triglyceridelowering agent will be initiated. Triglycerides will be reassessed at the end of the week, and temsirolimus will be resumed if the triglycerides level is reduced to Grade ≤2. If triglycerides remain at grade 3 or 4 levels, temsirolimus will be omitted another week, with serum triglycerides re-assessed one week later. If a patient's triglyceride levels remain at CTCAE grade 3-4 for two weeks despite triglyceride-lowering therapy, discontinue agent. If Grade 3 or 4 hypertriglyceridemia recurs after re-challenge, dose interruption will be managed as above, and the patient will resume therapy at a dose reduction of 2 dose levels if the hypertriglyceridemia resolves to a Grade ≤2 level within 2 weeks. |

TABLE 6B

Specific Dose Modifications for Pneumonitis.

| Adverse Event | NCI CTCAE grade | Temsirolimus |
|---|---|---|
| Polmunary/ Upper Respiratory | Pneumonitis | Patients with cough and dyspnea should have temsirolimus omitted pending investigation and permanently discontinued if the diagnosis is confirmed and thought to be related to temsirolimus |

TABLE 6C

Specific dose modifications for Hypersensitivity Reactions.

| Adverse Event | NCI CTCAE grade | Temsirolimus |
|---|---|---|
| Hypersensitivity Reactions | Grades 0-2 (eg flushing, skin rash, asymptomatic broncospasm | Slow or hold infusion. Give supportive treatment. Upon symptom resolution, may resume infusion-rate escalation at the investigator's discretion |
| | Grade 3 (eg symptomatic bronchospasm, requiring parenteral treatment, allergy related edema or angioedema | Discontinue infusion. Give supportive treatment. Upon symptom resolution, may resume infusion rate escalation, at investigator discretion. Note: If the same adverse event recurs with same severity, treatment must be permanently discontinued. |
| | Grade 4 (life threatening anaphylaxis) | Discontinue infusion immediately, treat symptoms aggressively, and do not restart drug. |

Example 6

Treatment Calendar

Baseline (pre-study) evaluations are to be conducted within 7 days prior to start of protocol therapy. Scans are done ≤4 weeks prior to the start of therapy. In the event that the patient's condition is deteriorating, laboratory evaluations are repeated within 48 hours prior to initiation of the next cycle of therapy. A cycle is 28 days long.

| | | Treatment Cycle (28 days) | | | | |
|---|---|---|---|---|---|---|
| | Pre-study | Day 1 | Day 8 | Day 15 | Day 22 | Off study |
| Inotuzumab Ozogamicin | | X | | | | |
| Temsirolimus | | X | X | X | X | |
| CD22 evaluation | X | | | | | |
| Demographics | X | | | | | |
| Medical history | X | | | | | |
| B-HCG[b] | X[b] | | | | | |
| Serological testing for Hepatitis B and C | X | | | | | |
| Concurrent meds | X[c] | X------------------------------------X | | | | |
| Physical exam | X | X | X | X | X | X |
| Vital signs (BP, Pulse, Respiration Rate) | X | X | X | X | X | X |
| Height | X | | | | | X |
| Weight | X | X | | | | X |
| Performance status | X | X | | | | X |
| CBC w/diff, plts | X | X | X | X | X | X |
| PT, INR, PTT | X | X | | | | |
| Serum chemistry[d] | X | X | X[e] | X[e] | X[e] | X |
| Hemoglobin A1C | X | | | | | |

-continued

|  | Pre-study | Treatment Cycle (28 days) | | | | Off study |
|---|---|---|---|---|---|---|
|  |  | Day 1 | Day 8 | Day 15 | Day 22 |  |
| EKG | X | X | | | | |
| Adverse event evaluation | | X---------------------------------------X | | | | X |
| Tumor measurements | X | Tumor measurements are repeated every 2 cycles Documentation (radiologic) must be provided for patients removed from study for progressive disease. | | | | X$^f$ |
| Radiologic evaluation | X | Radiologic measurements should be performed every 2 cycles. | | | | X$^f$ | a: Patients must be consented at least 4 weeks prior to study entry (registration) as they are required to use two forms of contraception as of 4 weeks prior to registration.
$^b$One serum pregnancy test (with a sensitivity of at least 25 mIU/mL) within 7 days prior to the first dose of study therapy
$^c$Concurrent medications recorded as of 30 days pre registration.
$^d$Albumin, alkaline phosphatase, total bilirubin, bicarbonate, BUN, calcium, chloride, creatinine, glucose, LDH, magnesium, phosphorus, potassium, total protein, SGOT[AST], SGPT[ALT], sodium, cholesterol, triglycerides.
$^e$Serum chemistry on days 8, 15 and 22 only on C1.
$^f$CT scans to be performed at baseline and every two cycles thereafter. Bone marrow aspirate and biopsy should be perfomed only in patients with known bone marrow lymphoma involvement.

Example 7

Measurement of Effect

Antitumor Effect:

For the purposes of this study, patients are re-evaluated for response every two cycles. Response and progression are evaluated in this study using the new Modified Response Criteria for Malignant Lymphoma. All patients are evaluabled for toxicity from the time of their first treatment with inotuzumab ozogamicin and temsirolimus. Only those patients who have measurable disease present at baseline, have received at least one cycle of therapy, and have had their disease re-evaluated are considered evaluable for response. These patients have their response classified according to the definitions stated below. (Note: Patients who exhibit objective disease progression prior to the end of cycle 1 are also considered evaluable.)

Disease Parameters:

Up to six of the largest dominant nodes or tumor masses selected according to all of the following:
1. Clearly measurable in at least two perpendicular dimensions at baseline. All nodal lesions are measured: >1.5 cm in greatest transverse diameter (GTD) regardless of short axis measurement, or, >1.0 cm in short axis regardless of the GTD measurement.
2. All extranodal lesions are measured ≥10 mm in the GTD and twice the reconstruction interval of the scan.
3. If possible, they are from disparate regions of the body.
4. They include mediastinal and retroperitoneal areas of disease whenever these sites are involved.
5. Extranodal lesions within the liver or spleen are at least 1.0 cm in two perpendicular dimensions.

Non-target lesions are qualitatively assessed at each subsequent time point. All of the sites of disease present at baseline and not classified as target lesions are classified as non-target lesions, including any measurable lesions that were not chosen as target lesions. Examples of non-target lesions include: all bone lesions, irrespective of the modality used to assess them; lymphangitis of the skin or lung; cystic lesions; splenomegaly and hepatomegaly; irradiated lesions; measurable lesions beyond the maximum number of six; groups of lesions that are small and numerous; and pleural/pericardial effusions and/or ascites For the study of the present invention, a significant increase in existing pleural effusions, ascites, or other fluid collections are considered sufficient evidence of progression and do not require cytological proof of malignancy. Effusions, ascites or other fluid collections are followed as non-target lesions.

Further, the existing effusions/ascites such as effusions, ascites or other fluid collections are followed as non-target lesions. At each time point, radiologists check for the presence or absence of effusions/ascites. If there is a significant volume increase in the absence of a benign etiology, progression is assessed. Significant new effusions, ascites or other fluid collections, which are radiographically suggestive of malignancy are recorded as new lesions.

Unable to Evaluate (UE) lesion category is reserved for target and non-target lesions that are deemed un-evaluable because 1) subsequent (post-baseline) exams had not been performed, 2) lesions could not be evaluated due to poor radiographic technique or poorly defined margins, or 3) lesions identified at baseline were not at a subsequent time point. Examples of UE lesions are a lung lesion in the hilum obstructing the bronchus and causing atelectasis of the lobe, or a hypodense liver lesion that becomes surrounded by fatty infiltration. In both examples the boundaries of the lesion can be difficult to distinguish. Every effort is made to assign measurements to lesions that develop less distinct margins because they become much smaller. Another example is the instance when lesions identified at baseline were not imaged at a subsequent time point unless the lesions are not imaged because of complete resolution. Lesions that cannot be measured or evaluated will be classified for that time point as UE. If a target lesion is classified as UE post-baseline, the SPD/area (whichever applies) of the target lesions cannot accurately be determined for that time point a response of CR, PR, or SD cannot be assigned for that time point and the response assessment will be UE unless unequivocal progression is determined on the basis of non-target or new lesions, or the evaluable target lesions. PD can be determined without evaluation of all sites of disease based on the GTD, area or SPD for target lesions, evaluation of unequivocal progression in non-target lesions or observation of a new lesion within the available radiographic or clinical assessments.

Any target lesion findings identified on baseline images, which at a subsequent time point decreases in size to <5 mm in any dimension, are categorized as Too Small To Measure (TSTM). The lesion, node or mass are assigned measurements of 5 mm×5 mm (for the GTD and the short axis) on the Source Document for the purpose of calculating the area. If that lesion increases in size to 5 mm in any dimension afterwards, its true size (GTD and short axis) should be recorded. The purpose of the assigned value for the measurement is the acknowledgment that small findings are not accurately measured.

Example 8

Response Criteria and Evaluation of Target Lesions

Complete Response (CR):
complete disappearance of all detectable clinical evidence of disease and disease-related symptoms if present prior to therapy. Further, the spleen and/or liver, if considered enlarged prior to therapy on the basis of a physical examination or CT scan, should not be palpable on physical examination and should be considered normal size by imaging studies, and nodules related to lymphoma should disappear. However, determination of splenic involvement is not always reliable because a spleen considered normal in size may still contain lymphoma, whereas an enlarged spleen may reflect variations in anatomy, blood volume, the use of hematopoietic growth factors, or causes other than lymphoma. If the bone marrow was involved by lymphoma prior to treatment, the infiltrate must have cleared on repeat bone marrow biopsy. The biopsy sample on which this determination is made must be adequate (>20 mm unilateral core). If the sample is indeterminate by morphology, it should be negative by immunohistochemistry. A sample that is negative by immunohistochemistry but demonstrating a small population of clonal lymphocytes by flow cytometry will be considered a CR until data become available demonstrating a clear difference in patient outcome.

Partial Response (PR):

1. a ≥50% decrease in sum of the product of the diameters (SPD) of up to 6 of the largest dominant nodes or nodal masses. These nodes or masses should be selected according to the following: (a) they should be clearly measurable in at least 2 perpendicular dimensions; (b) if possible they should be from disparate regions of the body; (c) they should include mediastinal and retroperitoneal areas of disease whenever these sites are involved. 2. No increase in the size of the other nodes, liver, or spleen. 3. Splenic and hepatic nodules must regress by ≥50% in their SPD or, for single nodules, in the greatest transverse diameter. 4. With the exception of splenic and hepatic nodules, involvement of other organs is usually assessable and no measurable disease should be present. Bone marrow assessment is irrelevant for determination of a PR if the sample was positive prior to treatment. However, if positive, the cell type should be specified (e.g. large-cell lymphoma or small neoplastic B cells). Patients who achieve a complete remission by the above criteria, but who have persistent morphologic bone marrow involvement will be considered partial responders. 6. No new sites of disease should be observed (e.g., nodes >1.5 cm in any axis). In patients with follicular lymphoma, a FDG-PET scan is only indicated with one or at most two residual masses that have regressed by more than 50% on CT; those with more than two residual lesions are unlikely to be FDG-PET negative and should be considered partial responders. At least a 30% decrease in the sum of the diameters of target lesions, taking as reference the baseline sum diameters.

Stable Disease (SD):

1. Failing to attain the criteria needed for a CR or PR, but not fulfilling those for progressive disease (see below).

Progressive Disease (PD):

Lymph nodes are considered abnormal in the long axis is >1.5 cm, regardless of the short axis. If a lymph node has a long axis of 1.1-1.5 cm, it should only be considered abnormal if its short axis is >1.0. Lymph nodes ≤1.0 cm by ≤1.0 cm will not be considered as abnormal for relapse or progressive disease. 1. Appearance of any new lesion more than 1.5 cm in any axis during or at the end of therapy, even if other lesions are decreasing in size. 2. At least a 50% increase from nadir in the sum of the product of the diameters (SPD) of any previously involved nodes, or in a single involved node, or the size of other lesions (e.g., splenic or hepatic nodules). To be considered progressive disease, a lymph node with a diameter of the short axis of less than 1.0 cm must increase by ≥50% and to a size of 1.5×1.5 cm or more than 1.5 cm in the long axis. 3. At least a 50% increase in the longest diameter of any single previously identified node more than 1 cm in its short axis. Measurable extranodal disease should be assessed in a manner similar to that for nodal disease. For these recommendations, the spleen is considered nodal disease. Neither sufficient shrinkage to qualify for PR nor sufficient increase to qualify for PD, taking as reference the smallest sum diameters while on study.

We claim:

1. A method of treating cancer, the method comprising the step of administering to a subject in need of such treatment, either simultaneously or sequentially, an effective amount of inotuzumab ozogamicin and temsirolimus, wherein the cancer is non-Hodgkin's lymphoma, and wherein inotuzumab ozogamicin is administered at a dose of 0.4 mg/m$^2$ to 1.8 mg/m$^2$ every 4 weeks for 6 cycles and temsirolimus is administered at a dose of 5 to 175 mg/week until disease progression.

2. The method of claim 1 wherein inotuzumab ozogamicin and temsirolimus are administered sequentially in either order.

3. The method of claim 1, wherein the temsirolimus dose is 5 mg per week.

* * * * *